(12) United States Patent
Maclure et al.

(10) Patent No.: US 11,246,588 B2
(45) Date of Patent: Feb. 15, 2022

(54) SUPERELASTIC BONE COMPRESSION STAPLE IN STAPLE SYSTEM

(71) Applicant: ORTHO SOLUTIONS HOLDINGS LIMITED, Littleton, CO (US)

(72) Inventors: Alister Maclure, Chelmsford (GB); Dustin Ducharme, Littleton, CO (US); Kevin Stamp, Sheffield (GB)

(73) Assignee: ORTHO SOLUTIONS HOLDINGS LIMITED, Littleton, CO (US)

( * ) Notice: Subject to any disclaimer, the term of this patent is extended or adjusted under 35 U.S.C. 154(b) by 162 days.

(21) Appl. No.: 16/457,193

(22) Filed: Jun. 28, 2019

(65) Prior Publication Data

US 2020/0000465 A1   Jan. 2, 2020

Related U.S. Application Data

(60) Provisional application No. 62/691,266, filed on Jun. 28, 2018.

(51) Int. Cl.
| | | |
|---|---|---|
| *A61B 17/064* | (2006.01) | |
| *A61B 17/068* | (2006.01) | |
| *A61B 17/72* | (2006.01) | |
| *A61B 17/00* | (2006.01) | |

(52) U.S. Cl.
CPC ........ *A61B 17/0644* (2013.01); *A61B 17/068* (2013.01); *A61B 17/0642* (2013.01); *A61B 17/7291* (2013.01); *A61B 2017/00862* (2013.01); *A61B 2017/00867* (2013.01); *A61B 2017/0641* (2013.01); *A61B 2017/0645* (2013.01)

(58) Field of Classification Search
CPC ..................... A61B 17/064; A61B 2017/0649
See application file for complete search history.

(56) References Cited

U.S. PATENT DOCUMENTS

| | | | | |
|---|---|---|---|---|
| 4,269,180 A | * | 5/1981 | Dall | A61B 17/82 606/281 |
| 4,278,091 A | * | 7/1981 | Borzone | A61B 17/0642 411/469 |
| 5,209,756 A | * | 5/1993 | Seedhom | A61B 17/0642 606/151 |
| 5,662,655 A | * | 9/1997 | Laboureau | A61B 17/0642 606/75 |
| 6,325,805 B1 | * | 12/2001 | Ogilvie | A61B 17/70 606/75 |
| 7,481,830 B2 | * | 1/2009 | Wall | A61B 17/7059 606/286 |

(Continued)

*Primary Examiner* — Zade Coley
(74) *Attorney, Agent, or Firm* — Hudak, Shunk & Farine Co. LPA

(57) ABSTRACT

The invention is a staple system comprising a primary staple having a bridge member including an opening and an offset and a first and second set of one or two joined to the bridge member and a secondary staple having a pair of legs and a bridge member received in the opening in the bridge member of the primary staple. In a second embodiment, the staple system includes a primary staple that receives a secondary staple having differing leg lengths and including a detent that inhibits the secondary staple from backing out and the shoulders of the staples are reinforced to account for compressive and torsional loads.

14 Claims, 13 Drawing Sheets

(56) References Cited

U.S. PATENT DOCUMENTS

| | | | | |
|---|---|---|---|---|
| 8,721,646 B2* | 5/2014 | Fox | .................... | A61B 17/0642 |
| | | | | 606/75 |
| 8,728,131 B2* | 5/2014 | Di Giacomo | ........ | A61B 17/809 |
| | | | | 606/297 |
| 9,034,037 B2* | 5/2015 | Fiere | .................. | A61B 17/0682 |
| | | | | 623/17.11 |
| 9,561,032 B2* | 2/2017 | Shelton, IV | ......... | A61B 17/064 |
| 10,299,842 B2* | 5/2019 | Hollis | .................... | A61B 17/84 |
| 2004/0073222 A1* | 4/2004 | Koseki | ............... | A61B 17/0642 |
| | | | | 606/75 |
| 2008/0161808 A1* | 7/2008 | Fox | .................... | A61B 17/0642 |
| | | | | 606/75 |
| 2009/0318977 A1* | 12/2009 | Di Giacomo | ........ | A61B 17/809 |
| | | | | 606/286 |
| 2014/0154236 A1* | 6/2014 | Hester | .................... | A61B 17/04 |
| | | | | 424/94.64 |
| 2017/0007305 A1* | 1/2017 | Hollis | ................ | A61B 17/8605 |
| 2017/0065275 A1* | 3/2017 | Cheney | ................ | A61B 17/064 |
| 2017/0181779 A1* | 6/2017 | Leither | ............. | A61B 17/8057 |
| 2017/0303978 A1* | 10/2017 | Palmer | ................ | A61B 17/0642 |
| 2019/0192140 A1* | 6/2019 | Ducharme | ........ | A61B 17/0682 |

* cited by examiner

SUPERELASTIC BONE COMPRESSION STAPLE IN STAPLE SYSTEM

FIELD OF THE INVENTION

The present invention relates to a room temperature superelastic bone compression staple system intended for bone fixation in the surgical management of fractures and reconstruction of the foot and hand.

BACKGROUND OF THE INVENTION

Initial bone staples were temperature activated memory staples, which were rendered obsolete through the adoption of mechanically activated room temperature superelastic Nitinol devices as the relevant materials technology advanced to the current state of the art.

Over 1.8 million orthopaedic trauma fixation procedures were performed in the US in 2016, which is expected to remain the fastest growing segment through to 2025 and is expected to reach over $4 billion by 2025, and the fastest growing part of this market is the staple fixation segment. The primary driver for growth is reportedly a reduced operating time as compared to screws, and plates.

While this growth demonstrates that orthopedic arts have accepted bone staples as an alternative and even a preferred fixation hardware to screws and bone plates for certain procedures, there remain issues and limitations to the designs presently available. While the latest generation of memory staples have improved rigidity and compressive capability when used alone or as adjunctive hardware, (which could improve outcomes for certain procedures, such as the Lapidus arthrodesis), it is still desirable to provide a stiffer and stronger construct and more reproducible surgical technique than the generally accepted perpendicular arrangement of legs and bridge used for example for a first metatarsophalangeal arthrodesis procedure. Additionally, the prior art devices are not optimal for fracture and osteotomy fixation of the hand and foot, including joint arthrodesis and to stabilize and dynamically compress bone fragments to facilitate osteosynthesis.

The superelastic materials used in the present invention provide interesting characteristics but come with some challenges as well for fabrication and to avoid stress in the device as used. For example, the material tends to be somewhat more brittle in compression so that configurations need to take these, as well as manufacturing concerns into account.

In response to these and other concerns, the present staple has a low-profile design to respect the economy of space in small bone procedures and further is designed for quick and efficient use, including removal following bone fusion. Additional issues with the prior art staples include problems with packaging, implant or instrument breakage, incompatibility with the staple inserter or other related instruments, lack of compression or sustained compression within the bone/implant construct, and difficulties with the instrument and implantation process.

A known risk with the prior art staples is associated with over-spreading the staple, which can over-stress the staple legs and have a deleterious effect on mechanical properties, recoverable strain and fatigue resistance. The present invention reduces this risk through design improvements achieved in manufacture of the staple and in the configuration of the legs and a resultant reinforcement of the leg/bridge interface.

The present staple system has a unique configuration that provides a low-profile implant system that is particularly well suited for small bone procedures and which allows additional compression and balanced at a fusion site. The staple is designed for permanent implantation or unlike prior art devices, for removal following bone fusion which can typically take 4-6 weeks while the patient is partially weight bearing. Specific instrumentation is provided for the removal procedure.

The staple system is particularly well-suited for use in small bone procedures, including in the mid-foot or the hand. It can be placed in dorsal or plantar positions, or medial or lateral positions, and is advantageous in avoiding dorsal gapping that can be a problem in other prior art devices.

The staple system is manufactured from ASTM F2063 room temperature superelastic (e.g., from 2 to up to 8%) Nitinol. (and it is understood that other shape memory materials can be used in this design).

SUMMARY OF THE INVENTION

The present invention relates to a superelastic Nitinol staple system having a primary staple with a plurality (i.e. one or two pairs of spaced legs) joined by a bridge member.

The system comprises a first or primary staple having a plurality of legs extending downwardly from a bridge member which includes an opening and an accommodation for a second or secondary staple member. One or both of the staples are fabricated by machining a blank to form a staple in the closed (converging legs) shape and the resulting staple(s) is mechanically deformed during use to induce the superelastic shape memory properties to compress bone segments and facilitate osteosynthesis. The primary staple has a bridge member preferably having a uniform thickness defined between an exterior and corresponding opposing interior surface.

In the first embodiment the bridge member is "off-set" meaning that it extends along an axis to form a "table-top" type of configuration having a double bent section to form parallel first and second segments. The "table top" is more obvious in the energized state in which the legs are substantially transverse to the bridge member. In this embodiment, the primary staple includes an offset, which can be a dog-leg (meaning that the bridge member bends at an angle of from 75° to 110°, i.e. 90°+/−5° or 10°, in a first direction and from 75° to 110°, i.e. 90°+/−5° or 10° in a second direction such that the bridge member has a first segment that is parallel to a second segment. This offset area of the bridge member further includes an opening that receives a secondary staple sized to fit within the opening along the length of the opening so that is can apply a compressive force to bone segments beneath the opening.

The bridge member further includes an opening or recess to accommodate a secondary staple having a bridge member connecting two legs to provide additional directed compression within the central portion of the primary staple. This provides a staple system having a low-profile configuration which suits implantation in the small bone environment, in particular for use in osteotomies, fusions or other osteo synthesis procedures. In the second embodiment of the staple system of the invention, the secondary staple advantageously has two barbed legs joined by a bridge member having a slotted or oval opening, and a primary staple sits over the secondary staple. The primary staple includes a bridge member having a central slotted opening or slot, bounded on either end by a cross member which forms the top of two leg members that extend downward from the bridge in a rounded shoulder. The underside of the bridge includes a groove or "trough" which is of a width and depth to accommodate the bridge of the secondary staple and the trough includes side walls that are chamfered to allow the bridge of the secondary staple to be eased into position.

In both embodiments, the primary staple has one to six legs (and preferably two to four) on either end of the bridge member. The legs may be joined to the bridge member by corner extensions which flow into the legs or may extend directly from the bridge for example from an inwardly curved recess in the ends of the bridge member. The legs preferably have a cross-sectional shape which helps to eliminate stress risers, for example, at the conjunction of the legs and bridge. One such shape is a FIVE-sided polygon, such as pentagon where another is an increased thickness from the end view at the leg/bridge juncture with smooth transitions into and out of the area of great thickness. The staple is designed for optional removal, so that while the staple may include texturing, ridges, or barbs to improve the hold in bone, the amount of mechanical interference is limited, for example by the provision of low ridges and on one only one or two surfaces of the legs, such as on the inner surface facing inward on the leg. Thus, the staple design permits easy removal.

In a second embodiment of the staple in staple system, the primary staple includes a slot in the bridge portion and a longitudinal trough that is designed to accommodate the secondary staple. The two staples are used in combination so as to balance compressive forces across a bone/bone interface, for example, by providing staples having differing leg lengths or cross-sectional area to generate differing forces. This is designed to avoid gapping at the proximal area of the staples and to balance the force in the direction of the length of the bridge but as applied in the transverse direction by the staple legs. An example of this advantage is to avoid dorsal gapping at the underside of the bridge where a single superelastic staple tends to draw the ends of the legs together and cause the top or near bridge portion of the attached bone segments to gap.

In the first embodiment, the bridge member of the staple joins a plurality of legs (optimally four, five or six) having a regular cross-section such as a rectangle, and optional texturing or barbs which increase in cross section traveling toward the bridge on one or more surfaces, and preferably the inside surface of the staple legs, to increase the anchoring of the legs in bone.

The staple is provided having a range of different bridge widths and lengths ranging from 10 mm to 25 mm and various leg lengths in the same range of length, so as to accommodate different fixation procedures in the forefoot, midfoot, rearfoot and hand. In the second embodiment, the primary staple has multiple legs and the secondary staple has only two legs. In both cases, the bridge members have an opening, and in the primary member, the slot is closed at either end by cross members. On the bottom side, this primary staple includes a recess or trough which has chamfers to accommodate the bridge of the secondary staple. In this version, the cross members are positioned at the outside edges of the bridge of the secondary staple so that the primary staple sits so low as possible over the secondary staple.

A further aspect of the invention illustrated in this version, is the provision of a more robust solution for stress loading, both in bending and torsional loads, at the internal shoulder or junction of the bridge member and the leg or legs. Specifically, the geometry is optimized for a more favorable stress distribution to offset the locations of maximum stress and utilize available geometry more efficiently. Thus, the design is provided with an increased volume of material at the apex of the shoulder, so for example, from 5% to 25%, and preferably from 10% to 15% increase in volume distributed in the middle 15%-40% of the radius of the shoulder area. This design tends to concentrate the strength at the approximate position of the maximum in vivo stress, and just above the implanted position. In turn, the new peak bending and torsional stresses coincide at the center of the bridge. Accordingly, openings are provided at the bridge of the secondary and primary staple designs that accommodate the stress, such as by stress shielding. This means that these opening have elongated geometries with ends that taper or converge as compared to being partially circular in outline.

Preferably, the staples are made by EDM wire in multiple planes with a gradual localized thickening at the staple shoulder which ends prior to the preferred point of implantation. The staples are manufactured in a flat or linear state, and then bent to the initial configuration with downward extending legs. Optimally, the staples are both supplied pre-assembled on an inserter or introducer in a sterile procedure pack which may contain disposable instrumentation. Further the system includes a drill guide that provides for optimal placement of the staples relative to each other (of the dual staple system).

DETAILED DESCRIPTION OF THE INVENTION

Figure 1:
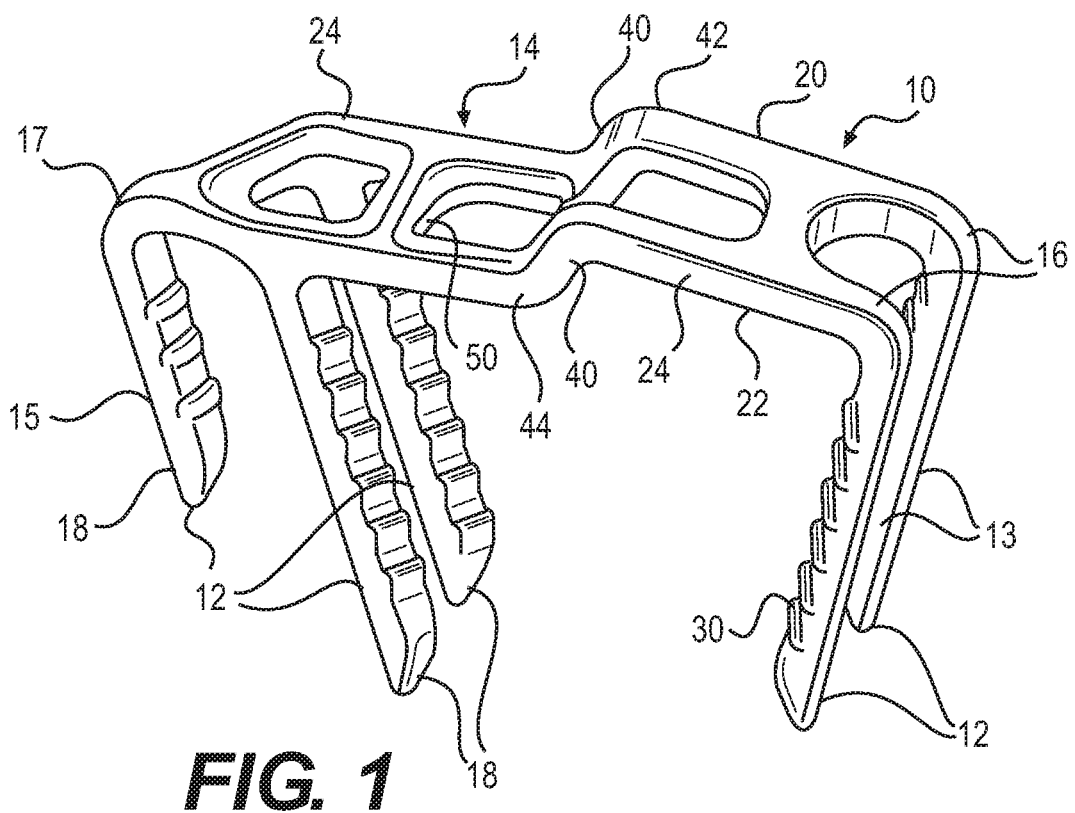
FIG. 1 shows a top perspective view of the primary staple in accordance with the present invention.
Figure 2:
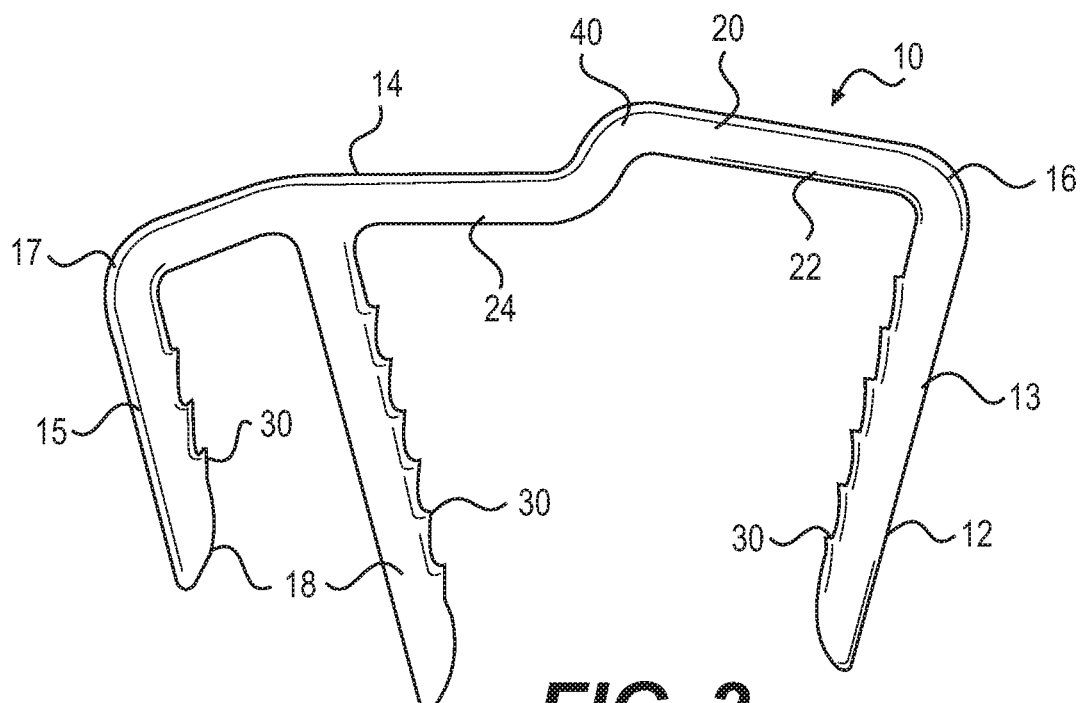
FIG. 2 shows a side view of the primary staple of FIG. 1.
Figure 3:
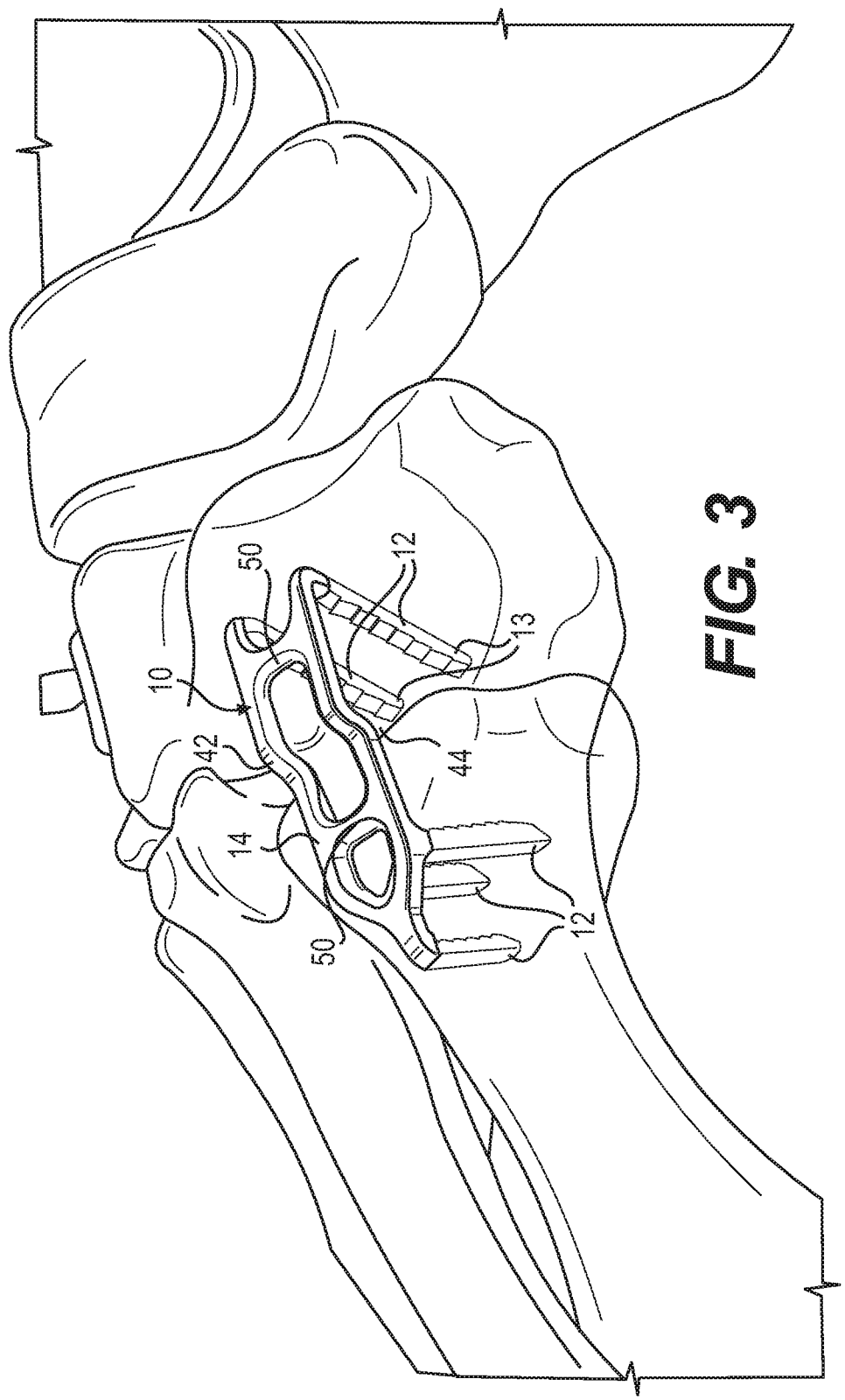
FIG. 3 shows a bottom side view of the primary staple of FIG. 1 in position in a foot.
Figure 4:
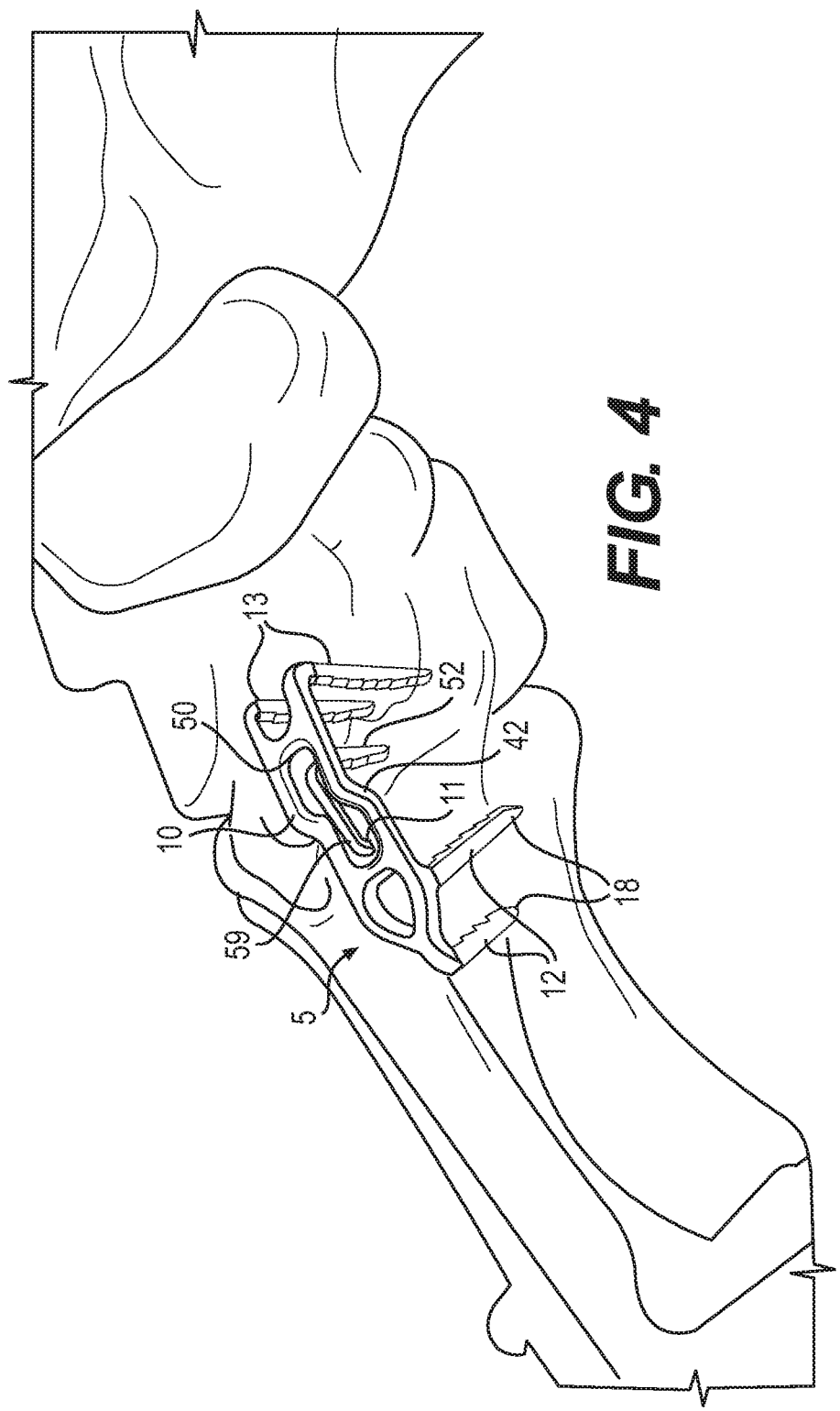
FIG. 4 shows a bottom side view of the staple system of the present invention in position in a foot.
Figure 5:
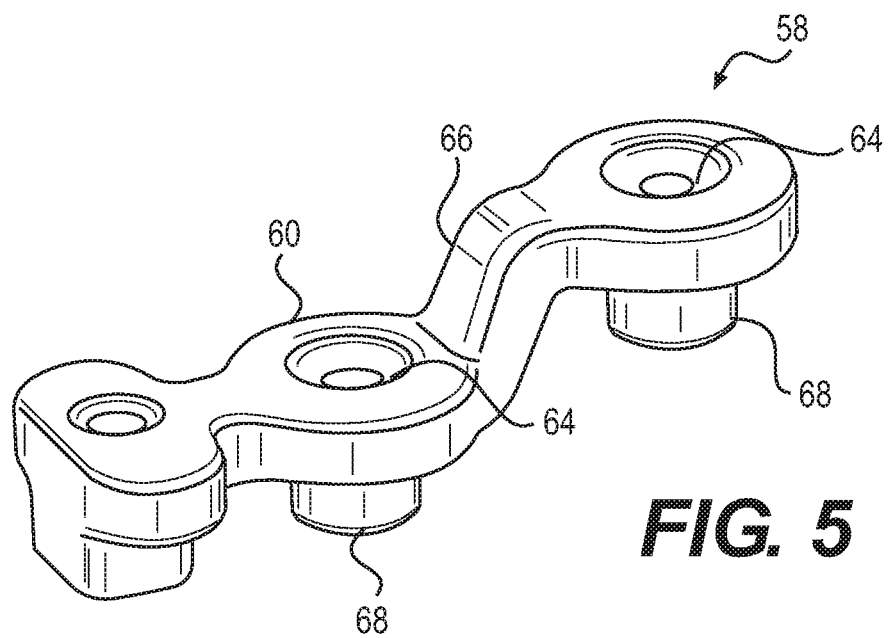
FIG. 5 shows a top side view of a drill guide for use with the secondary staple in staple system of the present invention.

The present invention relates to a room temperature superelastic Nitinol bone compression staple system 5 including a primary staple 10 and a secondary staple 11. The staple 10 has two or more, and preferably 2-6 legs and preferably 4, 5 or 6 legs 12 that will engage bones or bone segments through the cortical surfaces. The legs 12 are spaced apart from each other and joined together by bridge member 14 that extends across the area between legs at either end of the bridge member 14. As shown, the staple includes 5 legs, including a pair at one end of the bridge member 14 that are joined to transitional extensions 16 which fold or curve at an angle of from 75° to 90°, and preferably from 85° to 90° relative to a long axis of the bridge member. On the other end, the extensions 16 join to the bridge member 14 and the bridge member has an inwardly curved recess between the legs at the ends of the axis (when there are two legs on an end), and as well between the legs on the same sides of the axis. At the other end of the bridge member 14, the primary staple 10 has three legs 18 in a triangular configuration, with a pair of opposing legs 13 that extend away from the bridge member 14 at a t-intersection and a lead leg 15 that has a leg extension 17 similar to the transitional extensions 16 of the leg pair. This end of the bridge member further may include an opening.

The bridge member 14 has a top surface 20 and a bottom surface 22 which have corresponding shapes so that they are separated by a constant thickness for at least a portion, and preferably for at least 50%, and more preferably for at least 75% or even 90% of the surface area has a complex curving configuration. It extends along an axis preferably in a straight profile, but with a topography that can curve in either of two dimensions or optimally in both of two transverse directions. The shape includes two side edges 24, which may have an inwardly curving shape or may be represented by straight lines. The surfaces extending between the side edges 24 forming the top or outer surface and the bottom or inner surface of the bridge curve along the axis, in a shape that may define a portion of a circle, and they curve as well in a direction transverse to the axis.

The bridge member 14 further includes an offset area 40 which includes a first bend 42 roughly transverse to the length of the bridge member in the through or z direction, and spaced from that a second bend 44 which returns the bridge member to the first direction so as to form two parallel segments 46, 48. The offset area further includes an opening 50 which is sized and configured to accommodate a secondary staple fully within the opening to apply an additional compressive force below the opening to bone segments, and by "accommodate," it is meant for both the first and the second embodiment that the primary and the secondary staple bridges interface or interact so as to minimize any additional and extraneous material relative to the bone. Thus, the invention is designed for use in areas where the bone is close to the skin, and there may be little soft tissue to cover the implant.

The secondary staple 11 forms a part of the staple system, and comprises a pair of legs 52 joined at either end to a bridge member 54 where the legs extend transverse to the long axis of the bridge member in an activated state for insertion within the opening of the primary staple and after insertion they apply an inward force along the direction of the axis of that bridge member.

The staple legs can have an unusual and complex shape. While this can be a rectangle, they can form other polygons in cross section, such as pentagons, or they may more simply include areas of greater cross-sectional area to account for stresses in use. The legs may also include features 30 to help hold the legs in the bone, such as texturing, or ridges or barbs that help to hold the legs in position. Preferably, the surfaces of the legs that include this feature are opposing surfaces, such as surfaces that face an opposing leg. These ridges may include a series of spaced parallel ridges or alternating areas which in cross-section extend away from the base surface of the leg and return the base surface of the leg. Alternatively, the legs may include a series of grooves cut into the surface, or the legs may have a surface treatment, such as knurling, or cross-hatching. If they have ridges, the ridges may cover a portion of the vertical surface, such as 10-90%, and preferably from 25-50%. The ridges are lower profile than barbs, (for example only 0.25-2, and preferably 1+/−0.25 mm in height from the surface of the leg in order to permit earlier staple re-orientation and increased bone growth after removal.

Of a pair of opposing legs, either one or two legs may include these features. The legs have a cross-sectional configuration that provides for improved resistance to breaking as well as increased compressive forces, such as a polygonal shape that is not square. One preferred configuration is a rectangle. The staple may have two opposing legs, spaced apart from each other along the axis of the bridge member, or on one side it may have two legs, and one on the other, or it may have four legs which are situated to form a rectangle which circumscribes the bridge member. The staple is provided having a range of different bridge widths ranging from 10 mm to 25 mm and various leg lengths in the same range of length, so as to accommodate different fixation procedures in the forefoot, midfoot, rearfoot, ankle and hand.

Preferably, the staples are fabricated by machining or EDM wiring a Nitinol blank to form a staple in the closed (converging legs) shape and the resulting staple is mechanically deformed during use to "load" the staple, meaning to induce the superelastic shape memory properties to compress bone segments and facilitate osteosynthesis. In this state, the staple has legs extending at a substantially transverse direction to the axis of the bridge in order to allow the staple to be inserted into pre-drilled pilot holes in the bone. Optimally, the staple is supplied pre-assembled but not pre-loaded on an inserter or introducer that comes in a pre-sterilized pack.

Figure 6:
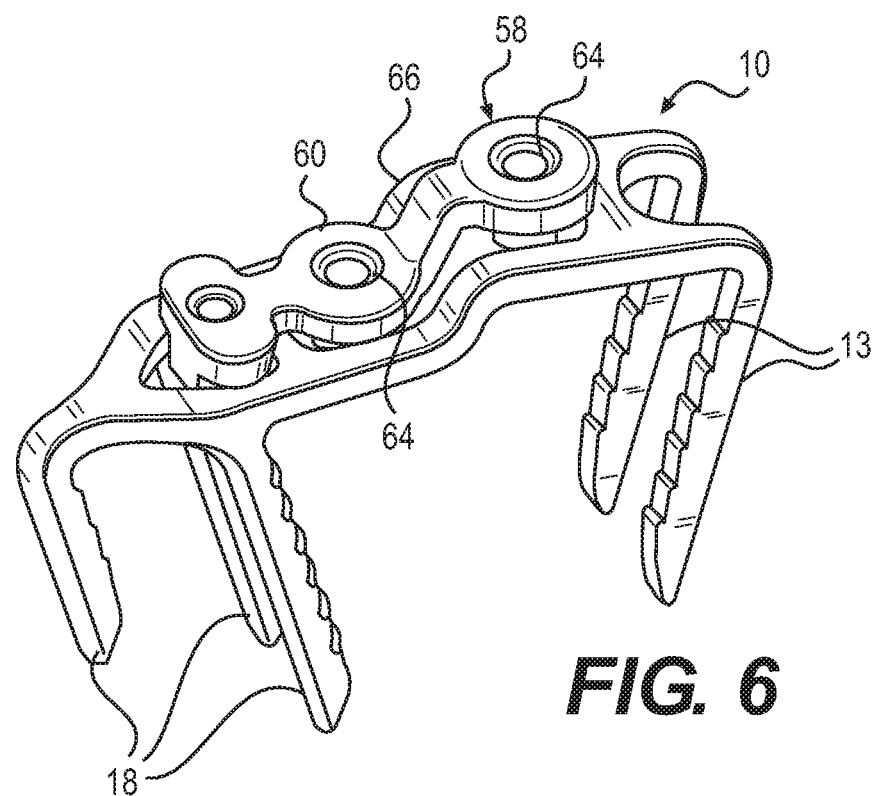
FIG. 6 shows a top side view of the secondary staple guide of FIG. 5 in place in a primary staple.
Figure 7:
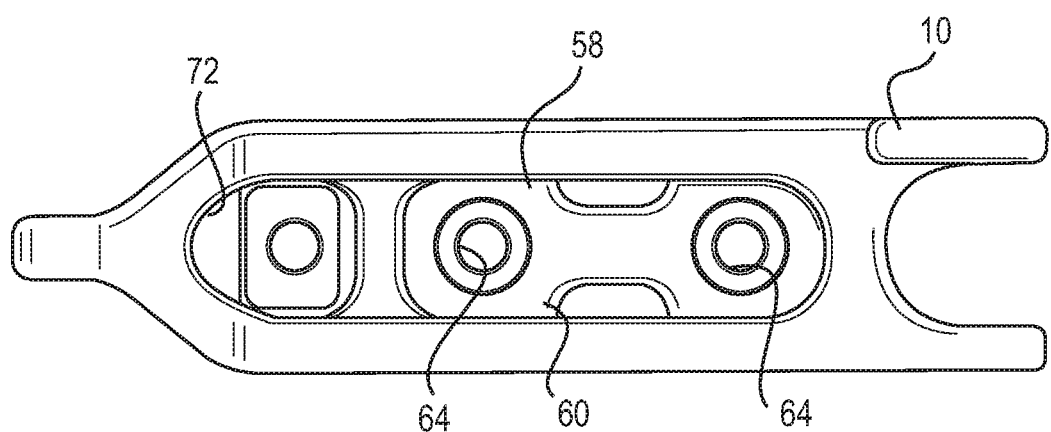
FIG. 7 is a bottom view of the secondary staple guide in position in a primary staple.
Figure 8:
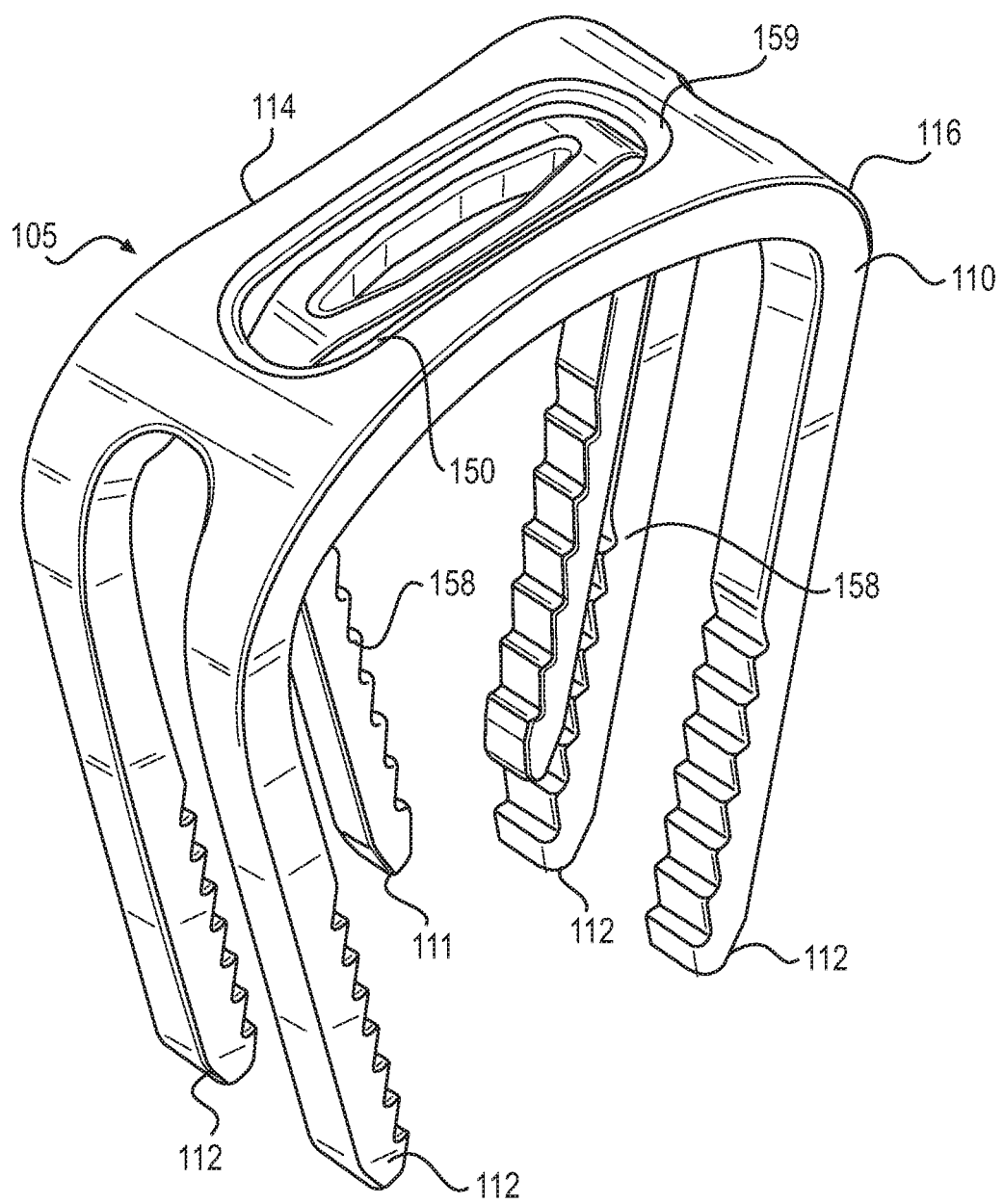
FIG. 8 shows a top side perspective view of a second embodiment of the staple in staple system in accordance with the present invention.
Figure 9:
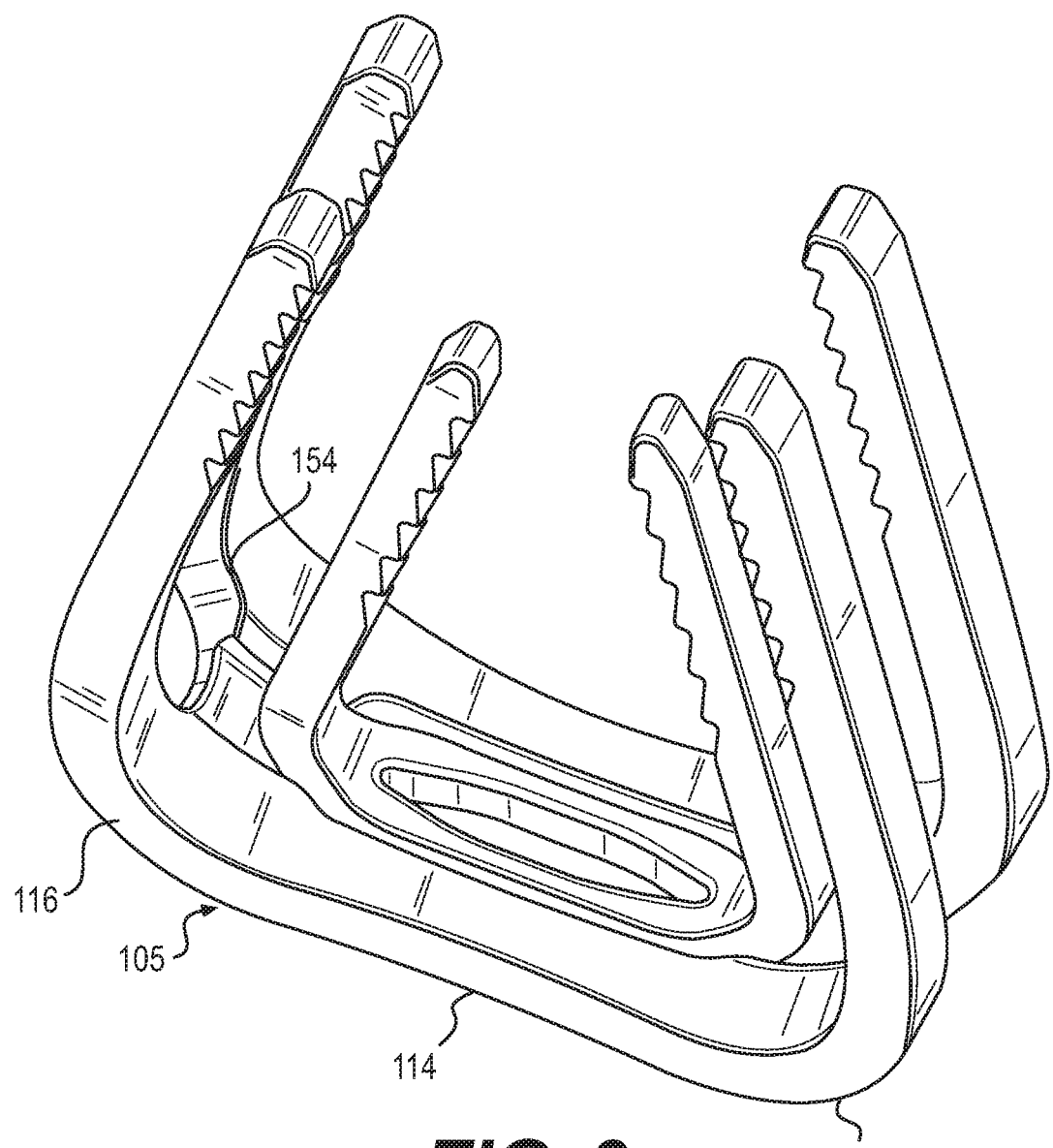
FIG. 9 shows a bottom side perspective view of the staple in staple system of FIG. 8.
Figure 10:
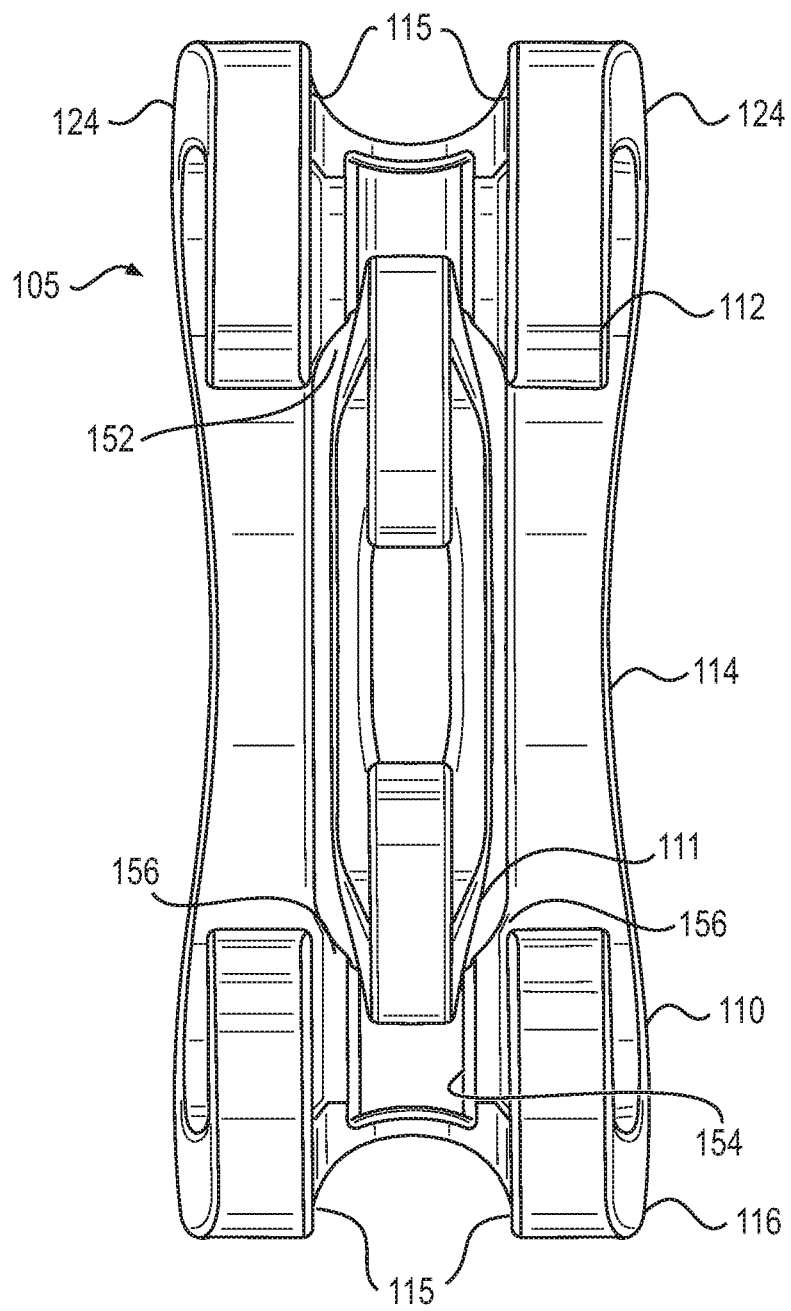
FIG. 10 shows a bottom view of the staple in staple system of FIG. 8.
Figure 11:
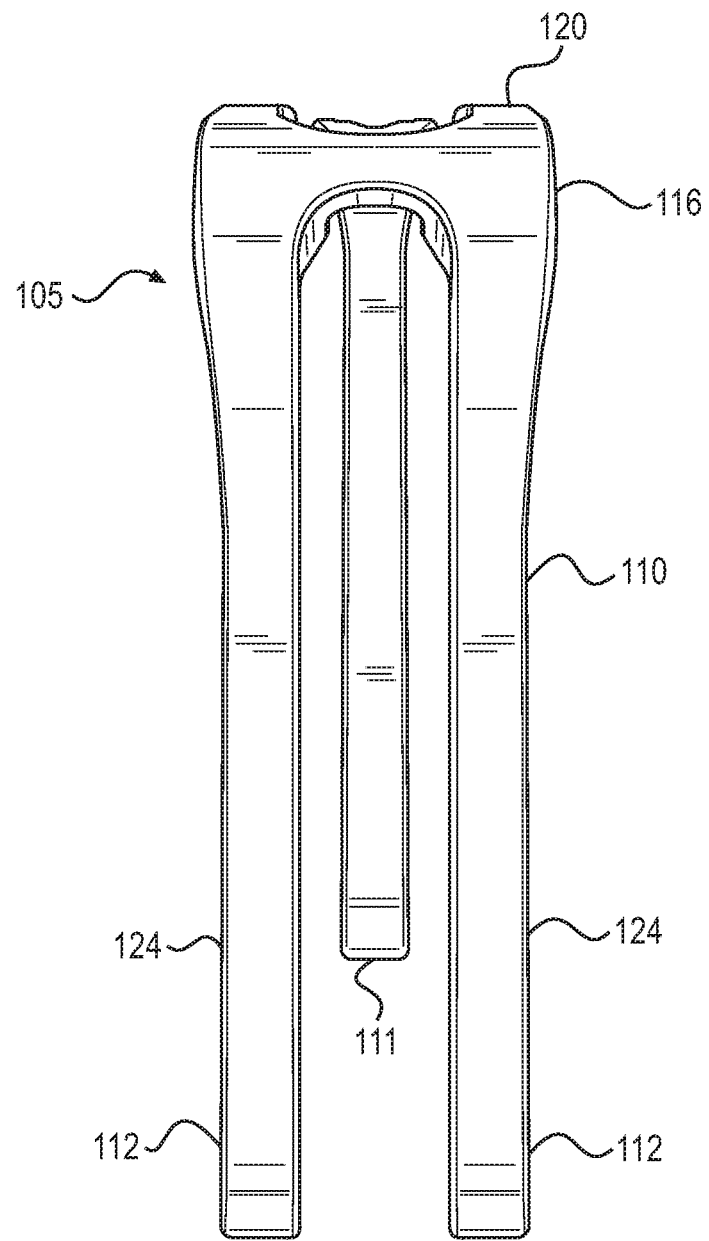
FIG. 11 shows an end view of the staple system of FIG. 8.
Figure 12:
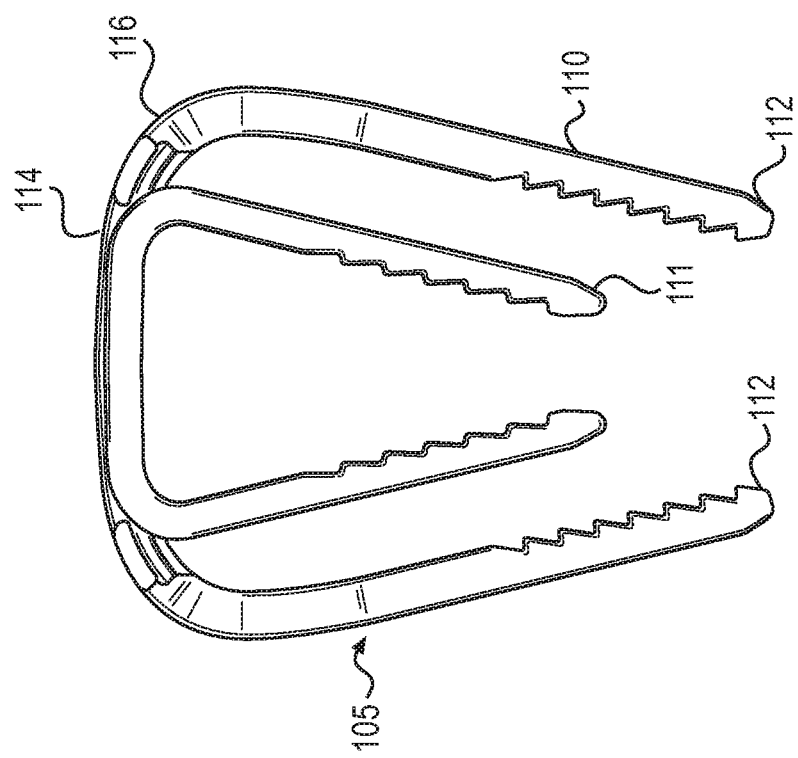
FIG. 12 shows a side view of the staple system of FIG. 8.
Figure 13:
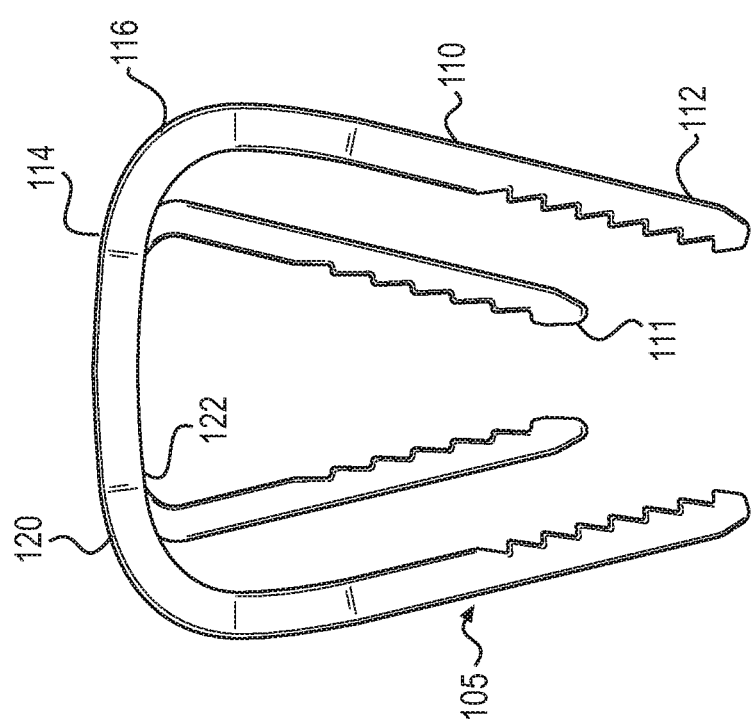
FIG. 13 shows the view of the staple in staple system of FIG. 12 in cross-section taken along the medial long axis of the bridge of the primary staple.
Figure 14:
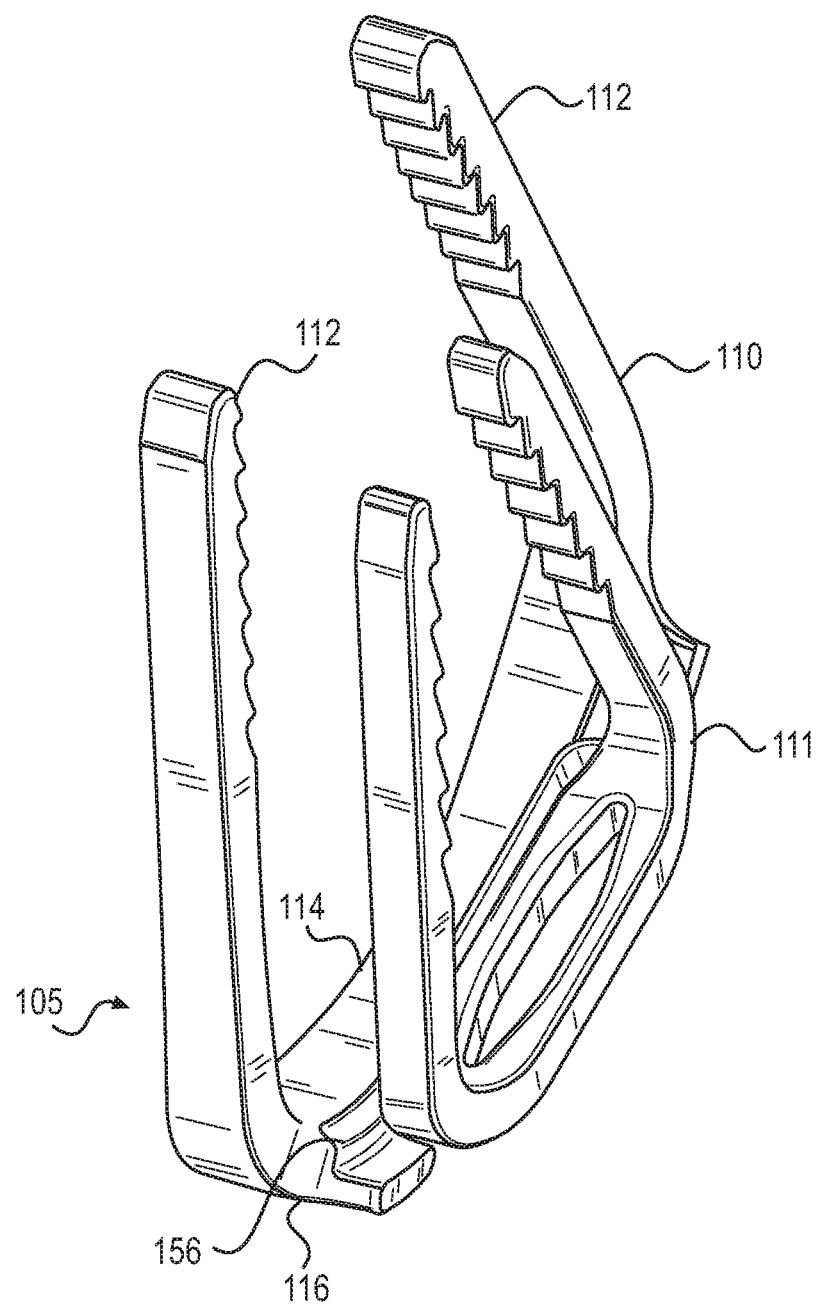
FIG. 14 shows a bottom side view of the staple in staple system of FIG. 13 also in cross-section.
Figure 15:
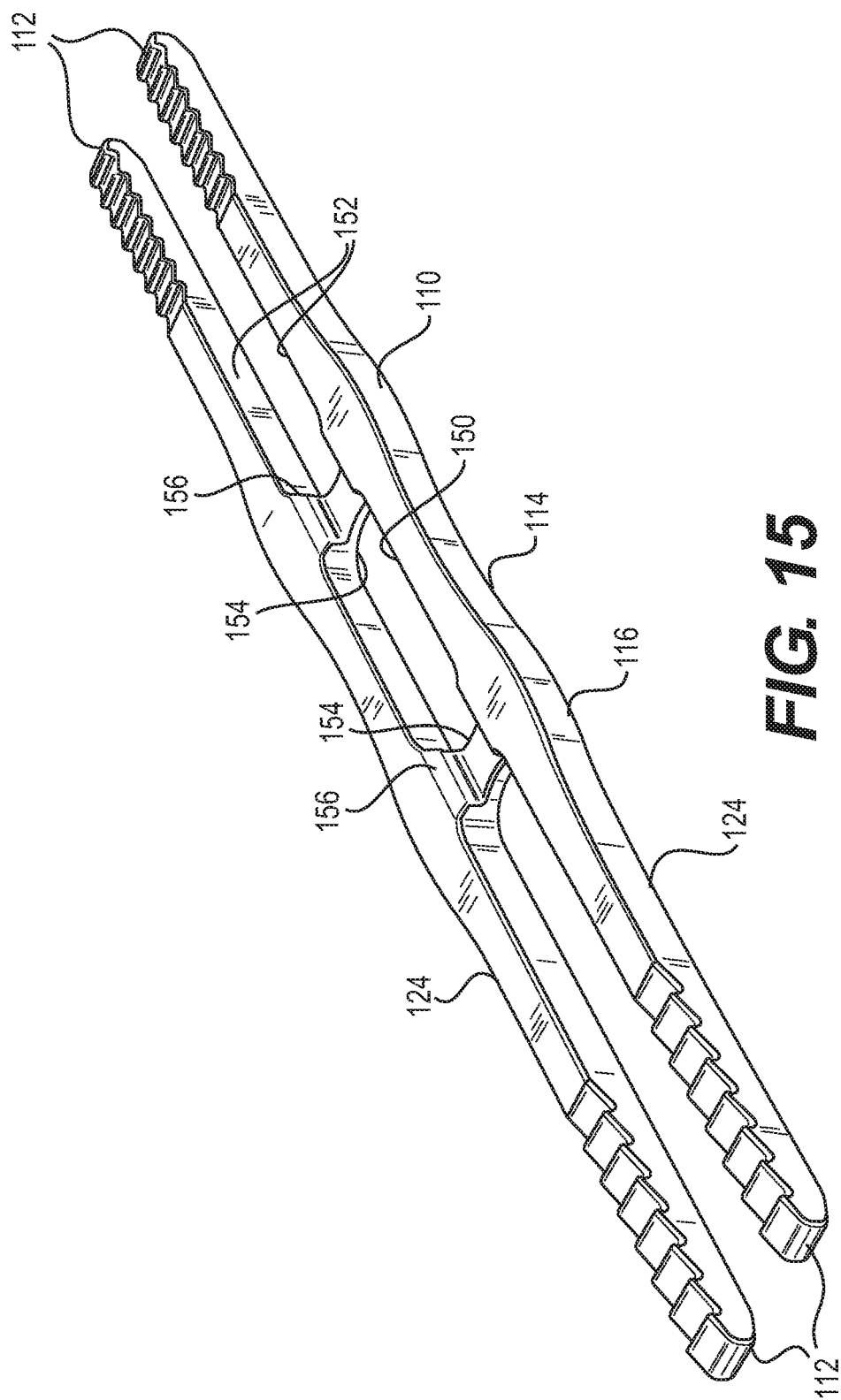
FIG. 15 shows a bottom side view of the primary staple of FIG. 8 after machining and prior to bending the legs in place in a primary staple.
Figure 16:
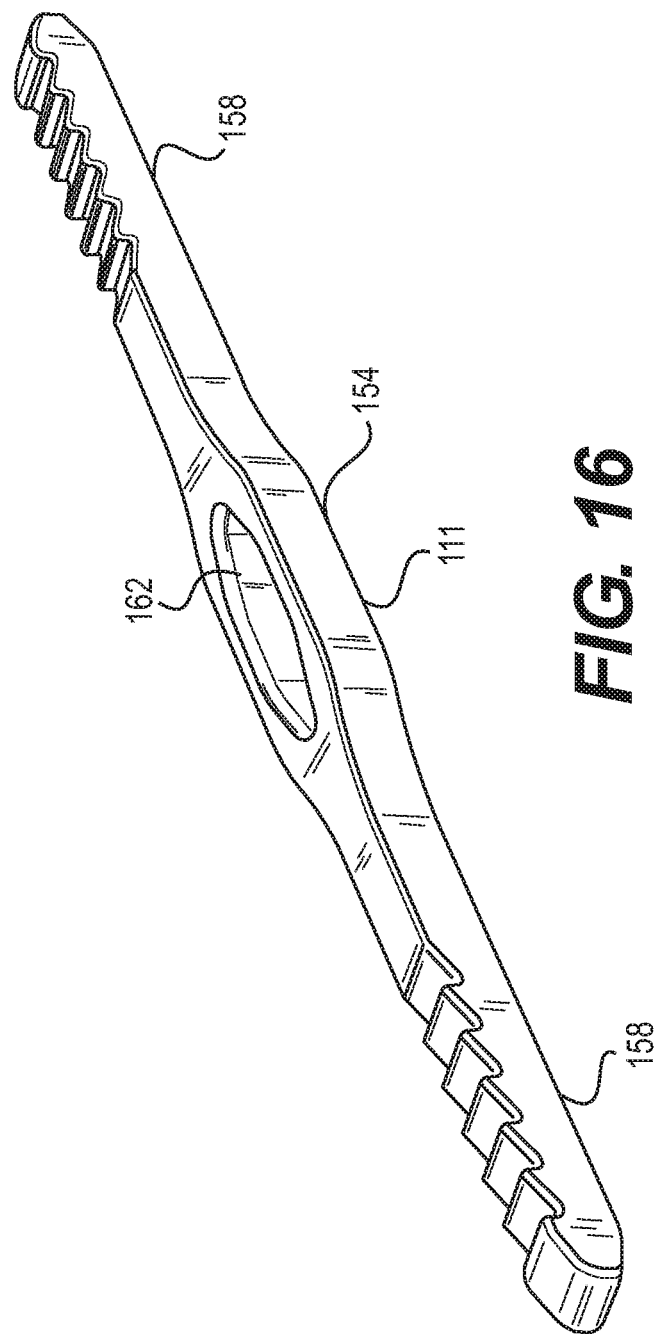
FIG. 16 shows a bottom side view of the secondary staple of FIG. 8 after machining and prior to bending the legs.

The invention further relates to a drill guide 58 that is configured for use with the staple system and can alternatively be used to position the secondary staple 11 within the recess 50 of the primary staple 10 (as is illustrated in FIGS. 6 and 7) or alternatively, position the primary staple about the secondary staple 11. The drill guide 58 includes a body 60 that has drill holes 64 aligned about an axis. The body 60 includes an offset 66 which corresponds to the offset in the primary staple. The drill holes include collars, 68 to help ensure a sufficient length of guidance for the drill. In addition, a front placement boss 70 can help to anchor the drill guide in a front fenestration 72 within the primary staple 10.

The present system is illustrated for use in a Lapidus procedure in the first metatarsal cuneiform joint of a foot. In this procedure, an incision is made to expose the surgical site, and the bone is prepared at a fusion site, for example by debriding or osteotomy and the bones are held in position, such as by k-wires. Holes are drilled for the legs of the primary staple, and the staple is activated in an inserter by opening the legs to a transverse position for insertion. The staple is tamped into position and removed from the inserter whereby the legs return to an angle to apply compression across the fusion site. The drill guide is position relative to the primary staple, here within a recess for the secondary staple, and holes are drilled for the secondary staple. The drill guide is removed, and the secondary staple is activated so that the legs are perpendicular for insertion, the secondary staple is inserted, and removed from the inserter so that the legs can also apply compression across the bone/bone interface.

In a second embodiment of the present invention shown in FIGS. 8-16 the staple in staple system relates to a room temperature superelastic Nitinol bone compression staple system 105 including a primary staple 110 and a secondary staple 111. The primary staple 110 has two or more, and preferably 2-6 legs and preferably 4, 112 that will engage bones or bone segments through the cortical surfaces. The legs 112 are spaced apart from each other and joined together by bridge member 114 that extends across the area between legs at either end of the bridge member 114. As shown, the primary staple 110 includes 4 legs, including a pair at each end of the bridge member 14 that are joined at radiused shoulders portions 116 which fold or curve at an angle of from 75° to 90°, and preferably from 85° to 90° relative to a long axis of the bridge member. On both ends, the staple is symmetrical about the long axis of the bridge and the shoulder portions 116 join to the bridge member 114 and the bridge member has an inwardly curved recess 115 between the legs at the ends of the axis of the bridge member 114. The shoulder portions curve gently outward along the side edges so as to increase the volume at the radiused area as can be best viewed in FIGS. 8-11 and 14-15. As FIG. 15, in particular shows, the shoulders are widened by 5-20%+/−4%, along the length of the side portion to account for an arc of from 15-40 degrees or the bend (again +/−10%).

The bridge member 114 has a top surface 120 and a bottom surface 122 which have corresponding shapes so that they are separated by a constant thickness for at least a portion, and preferably for at least 50%, and more preferably for at least 75% or even 90% of the surface area has a radiused or circular curving configuration. It extends along an axis preferably in a straight profile, but with a topography that can curve in a single or two dimensions, such as in both of two transverse directions. The shape includes two side edges 124, which may have an inwardly curving shape or may be represented by straight lines. The surfaces extending between the side edges 124 forming the top or outer surface and the bottom or inner surface of the bridge curve along the axis, in a shape that may define a portion of a circle, and they curve as well in a direction transverse to the axis.

The bridge member 114 further includes an opening 150 which is sized and configured to accommodate the secondary staple 111 fully within the opening to apply an additional compressive force below the opening to bone segments. More particularly, the primary staple 110 includes a trough 152 or elongated recess along the length of the bridge member 114 which extends across a pair of transverse connectors 154. The opening 150 is rounded and elongated at either opposing end which accommodates the end shoulder sections of the secondary staple, preferably so that the secondary staple avoids contact with the primary staple but resides fully within the opening. The trough 152 includes chamfered edges 156 which help to guide the secondary staple to seat it within the opening and trough. The transverse connectors are configured to interact with the top surface of the shoulder portions of the secondary staple to retain the secondary staple in the bone, or to keep it from backing out of position in the bone.

The secondary staple 111 forms a second part of the staple system, and comprises a one or two legs 158 joined at either end to a bridge member 159 having a central elongated diamond shaped opening 162 to increase the volume of the material at the shoulder junction. The legs extend transverse to the long axis of the bridge member in an activated state for insertion within the opening of the primary staple and after insertion they apply an inward force along the direction of the axis of that bridge member. As in the first embodiment, staple legs can have an unusual and complex shape. While this can be a rectangle, they can form other polygons in cross section, such as pentagons. The legs may also include features 30 to help hold the legs in the bone, such as texturing, or ridges or barbs that help to hold the legs in position. Preferably, the surfaces of the legs that include this feature are opposing surfaces, such as surfaces that face an opposing leg.

What is claimed is:

1. A staple system, comprising:
a primary superelastic staple having a bridge member having a top surface and an opposing bottom surface defining a thickness between and the bridge member having a long axis extending between a first end and a second end including a slotted opening along the long axis between the first end and the second end and being configured by the inclusion of a trough on the bottom surface having a width and depth to accommodate a bridge member of a secondary staple in a co-planar orientation, and at least a first leg at the first end extending away from and joined to the bridge member through a first shoulder member and at least a second leg at the second end extending away from and joined to the bridge member through a second shoulder member so as to converge at a distal end toward the first leg in a relaxed state; and
a secondary superelastic staple having at least a pair of legs each joined to to the bridge member through a shoulder so as to converge toward each other at a distal end in a relaxed state and the bridge member being received within the trough of the primary staple, and the pair of legs of the secondary superelastic staple being shorter than the legs of the primary superelastic staple whereby a compressive force is applied inward in the direction of the long axis by the secondary superelastic staple which balances a compressive force applied inward in the direction of the long axis by the primary staple.

2. A staple as set forth in claim 1, wherein the bridge member includes an offset having a first bend and a second bend.

3. A staple as set forth in claim 1, wherein the primary staple has between two and six legs.

4. A staple as set forth in claim 1, wherein the primary staple has a first set of legs which extend from one end of the bridge member and a second set of legs that extend from the second end of the bridge member.

5. A staple as set forth in claim 4, wherein one of the first or second set of legs includes three legs.

6. A staple as set forth in claim 1, wherein the superelastic material is Nitinol.

7. A staple has set forth in claim 1, wherein the material volume of the primary staple is increased at the first shoulder member and the second shoulder member.

8. A staple as set forth in claim 1, wherein the primary staple bridge top surface and the primary staple bridge bottom surface have a maximum thickness and the bottom surface trough is configured to fully accommodate the bridge of the secondary staple such that a top surface of the secondary staple does not extend beyond the maximum thickness of the primary staple bridge top surface.

9. A staple system, comprising:

a primary staple comprising a bridge member having a top surface and an opposing bottom surface defining a thickness between and the bridge member having a long axis and having an opening and a first set of a first leg joined by a shoulder member to the bridge member at a first end of the bridge member along the axis and a second leg joined by a shoulder member to a second end of the bridge member spaced apart along the axis from the first end of the bridge member where each set of legs applies an inward force after insertion toward the opposite set of legs along the direction of the long axis; and a secondary staple received in the opening and which is superelastic and has a secondary staple bridge member and at least a pair of secondary staple legs each joined by a shoulder member to the secondary staple bridge member so as to extend from the bridge member and where each of the secondary staple legs applies an inward force after insertion toward the opposite secondary staple leg along the direction of the long axis, and the secondary staple legs are not the same length as the primary staple legs so as to balance the forces generated by the primary staple legs and the secondary staple legs and the bottom surface has a trough configured to fully accommodate the bridge of the secondary staple in a co-planar orientation such that a top surface of the secondary staple does not extend beyond the maximum thickness of the primary staple bridge top surface, and the trough includes side walls that are chamfered to allow the bridge of the secondary staple to be eased into position.

10. A staple as set forth in claim 9, wherein two of the sets of first legs and the second legs include an engagement feature.

11. A staple as set forth in claim 10, wherein the engagement feature is a plurality of ridges.

12. A staple system as set forth in claim 9, further including a drill guide for the secondary staple.

13. A staple system as set forth in claim 12, wherein the drill guide is configured to guide the openings to receive the legs of one of the staples relative to the other.

14. A staple system as set forth in claim 13, wherein the primary bridge member includes an offset and the secondary staple includes an offset that corresponds to the offset of the primary bridge member.

* * * * *